United States Patent
Powers

(10) Patent No.: US 9,795,799 B2
(45) Date of Patent: Oct. 24, 2017

(54) AED HAVING MANDATORY PAUSE FOR ADMINISTRATING CPR

(75) Inventor: Daniel J. Powers, Issaquah, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 2092 days.

(21) Appl. No.: 11/917,511

(22) PCT Filed: Jun. 13, 2006

(86) PCT No.: PCT/IB2006/051898
§ 371 (c)(1),
(2), (4) Date: Dec. 14, 2007

(87) PCT Pub. No.: WO2006/136975
PCT Pub. Date: Dec. 28, 2006

(65) Prior Publication Data
US 2008/0215103 A1   Sep. 4, 2008

Related U.S. Application Data

(60) Provisional application No. 60/693,646, filed on Jun. 24, 2005, provisional application No. 60/737,187, filed on Nov. 16, 2005.

(51) Int. Cl.
*A61N 1/39* (2006.01)

(52) U.S. Cl.
CPC ......... *A61N 1/3987* (2013.01); *A61N 1/3925* (2013.01)

(58) Field of Classification Search
CPC ........................... A61N 1/3987; A61N 1/3925

USPC ........................................ 607/4–8
See application file for complete search history.

(56) References Cited

U.S. PATENT DOCUMENTS

| | | | | |
|---|---|---|---|---|
| 4,619,265 A | * | 10/1986 | Morgan et al. | 607/6 |
| 5,097,830 A | * | 3/1992 | Eikefjord et al. | 607/8 |
| 5,919,212 A | * | 7/1999 | Olson et al. | 607/5 |
| 6,314,320 B1 | | 11/2001 | Powers et al. | |
| 6,356,785 B1 | * | 3/2002 | Snyder et al. | 607/5 |
| 6,405,083 B1 | * | 6/2002 | Rockwell et al. | 607/5 |
| 6,697,671 B1 | | 2/2004 | Nova et al. | |
| 2003/0109790 A1 | * | 6/2003 | Stickney et al. | 600/500 |
| 2006/0116724 A1 | * | 6/2006 | Snyder | 607/5 |

FOREIGN PATENT DOCUMENTS

| | | |
|---|---|---|
| WO | 02/072197 A2 | 9/2002 |
| WO | 2004/054656 A | 7/2004 |

OTHER PUBLICATIONS

Philips:"The Importance of CPR While Using an Automated External Defibrillator"; Brochure on Heartstart Defibrillator's, 3 Page Document, Nov. 1, 2003.

* cited by examiner

*Primary Examiner* — Christopher D Koharski
*Assistant Examiner* — Roland Dinga

(57) ABSTRACT

A system and method are described for delivering electrotherapy to a patient that includes delivering electrotherapy to defibrillate the patient and providing at least one non-interruptible time period for administration of CPR prior to entering a monitor mode during which a patient cardiac signal is monitored for indication of a shockable rhythm.

5 Claims, 7 Drawing Sheets

AED HAVING MANDATORY PAUSE FOR ADMINISTRATING CPR

The invention generally relates to medical equipment, and more particularly, to automatic external defibrillators providing combined monitor and CPR pause modes of operation.

Defibrillators deliver a high-amplitude current impulse to the heart in order to restore normal cardiac rhythm and contractile function in patients who are experiencing arrhythmia, such as ventricular fibrillation ("VF") or ventricular tachycardia ("VT") that is not accompanied by a palpable pulse. There are many classes of defibrillators, including manual defibrillators and automatic external defibrillators ("AEDs"). AEDs differ from manual defibrillators in that AEDs can automatically analyze patient electrocardiogram ("ECG") rhythm to determine if defibrillation is necessary. In nearly all AED designs, the user is prompted to press a shock button to deliver the defibrillation shock to the patient.

AEDs are typically configured to provide a user with visual or audio prompts to carry out a medical protocol that includes both delivery of electrotherapy as well as performing cardio-pulmonary resuscitation ("CPR"). FIG. 2 illustrates a "monitor mode" of operation 200 for an AED that includes a CPR protocol. Following attachment of the electrodes to the patient, the AED analyzes the patient's cardiac rhythm at step 202. During the analysis, the AED is precharged in preparation for delivery of electrotherapy. Based on the analysis, a determination is made at step 204 whether to advise the delivery of electrotherapy. If the analysis reveals a "shockable rhythm" in the patient's cardiac rhythm, delivery of electrotherapy is advised and at step 206, the AED is fully charged and a defibrillation pulse is delivered to resuscitate the patient in response to the user pressing the shock button on the AED. This sequence can be repeated two additional times if the patient has not been resuscitated and a shockable rhythm is detected, resulting in a total delivery of three shocks.

When the shock sequence is completed the AED enters a monitoring mode and continues to analyze the ECG, looking for a shockable rhythm. As part of the medical protocol, it is recommended that CPR is administered after the series of defibrillation pulses have been delivered and hence CPR is usually performed during this monitoring period. As CPR is being performed, audio and/or visual prompts are used to instruct the user to perform CPR. Typically, the CPR pause period is on the order of one minute or more. At the completion of CPR the ECG continues to be analyzed at 214 for a shockable rhythm. If a shockable rhythm is detected a shock is advised and delivered, but if no shock is advised the AED is disarmed (discharged) at 216 and monitoring continues at 202. However, it is common for patients to lapse back into arrhythmia during the monitoring period after only a short period of CPR. When this happens the relapse is immediately detected by the monitoring mode and CPR is interrupted as the AED begins to charge for shock delivery. This sequence of shock delivery, entering a monitoring mode, beginning CPR, and prematurely ending the CPR period can be repeated for as long as a return to arrhythmia is detected by monitoring during CPR. In some cases artifacts from the CPR compressions can be detected by the ECG processor and also cause a premature termination of CPR delivery. The patient is never afforded a full interval of early CPR treatment.

Another mode of AED operation is the "CPR pause" mode illustrated in FIG. 3. Since studies have shown that early CPR can play a critical role in patient recovery, this mode is becoming increasingly popular as an AED setup. The CPR pause mode begins with the same rhythm analysis 202, shock advised decision 204 and shock sequence delivery 206, 208 as in the monitoring mode. At the end of the shock sequence 208 or when a shock is not advised at 204, the AED enters a full CPR pause period at 212. Toward the end of the CPR pause period the AED is precharged in preparation for a possible post-CPR shock delivery. At the conclusion of the CPR pause the ECG is again analyzed for a shockable rhythm at 214 and if none is detected, the precharge is disarmed at 216 and the process returns to the initial rhythm analysis step 202. A problem with this process can arise when a patient has been resuscitated and the AED is being used to monitor for a subsequent occurrence of arrhythmia. In the procedure used by many commercial airlines, for example, it is common practice to leave the AED attached to the patient to continue to perform monitoring until the plane lands and professional medical personnel can assume control of the patient. In the CPR pause mode, the AED will continue to enter CPR pause periods, precharge the high-voltage circuitry, then discharge the high-voltage circuitry when no shockable rhythm has been detected. A problem with this operation is that battery life of the AED can be significantly shortened. As previously discussed, during the CPR pause period at step 212, the AED is typically precharged in preparation for delivery of electrotherapy, if necessary. However, as also previously discussed, if a shockable rhythm is not detected at step 214, the AED is disarmed, which includes discharging the precharge from step 212. The process, shown in FIG. 3 as "cycle A," can continue to repeat, including the precharge/discharge process cycle which shortens battery life significantly. The detrimental effects on battery life become especially acute for a stable patient, because the user observes that the battery is quickly depleting even though patient is receiving no electrotherapy. In the worst case, the battery is depleted to such an extent that it can no longer provide sufficient charge for the AED to deliver a defibrillation pulse if one is necessary at a later time. Furthermore, each recharge will be accompanied by worrisome commands such as "do not touch the patient," the command generally delivered to the rescuer and bystanders when the AED is charging its high voltage circuitry. Accordingly it is desirable to prevent such needless depletion of the AED battery and the delivery of troubling instructions which can be avoided.

Therefore, there is a need for an AED that initiates a CPR pause early in a cardiac rescue and which is sufficient to deliver the necessary CPR treatment and which, when employed for monitoring after resuscitation, does not needlessly precharge and discharge and unnecessarily deplete its battery.

One aspect of the invention provides a method for providing electrotherapy that includes analyzing a cardiac signal for a shockable rhythm, delivering electrotherapy if a shockable rhythm exists and pausing for a non-interruptible CPR period after analysis of the cardiac signal. The cardiac signal is re-analyzed for a shockable rhythm and the cardiac signal is monitored without precharging an electrotherapy high-voltage energy source.

Another aspect of the invention provides a method for providing electrotherapy to a patient using an automatic external defibrillator. The method includes analyzing the patient ECG to determine if delivery of electrotherapy is advisable and delivering electrotherapy to the patient if electrotherapy is advised. The method further includes, for a first occurrence of electrotherapy not advised, pausing for a uninterruptible time period to allow administration of CPR and analyzing the patient ECG again to determine if delivery of electrotherapy is advisable, and for a second consecutive occurrence of electrotherapy not advised, monitoring the patient ECG for indication of a shockable rhythm.

Another aspect of the invention provides a method for delivering electrotherapy to a patient that includes delivering electrotherapy to defibrillate the patient and providing at least one non-interruptible time period for administration of CPR prior to entering a monitor mode during which a patient cardiac signal is monitored for indication of a shockable rhythm.

Another aspect of the invention provides an automatic external defibrillator having a cardiac signal analyzer, a monitoring mode of operation, a CPR pause mode of operation, and a controller for selecting one of the monitoring mode and the CPR pause mode based on an output from the cardiac signal analyzer. Another aspect of the invention provides an automatic external defibrillator having a processing circuit operable to analyze a cardiac signal and further having a control circuit operable to provide at least one non-interruptible time period for administration of CPR prior to entering a monitor mode during which the cardiac signal is monitored for indication of a shockable rhythm.

Certain details are set forth below to provide a sufficient understanding of the invention. However, it will be clear to one skilled in the art that the invention may be practiced without these particular details. Moreover, the particular embodiments of the present invention described herein are provided by way of example and should not be used to limit the scope of the invention to these particular embodiments. In other instances, well-known circuits, control signals, timing protocols, and software operations have not been shown in detail in order to avoid unnecessarily obscuring the invention.

Figure 1:
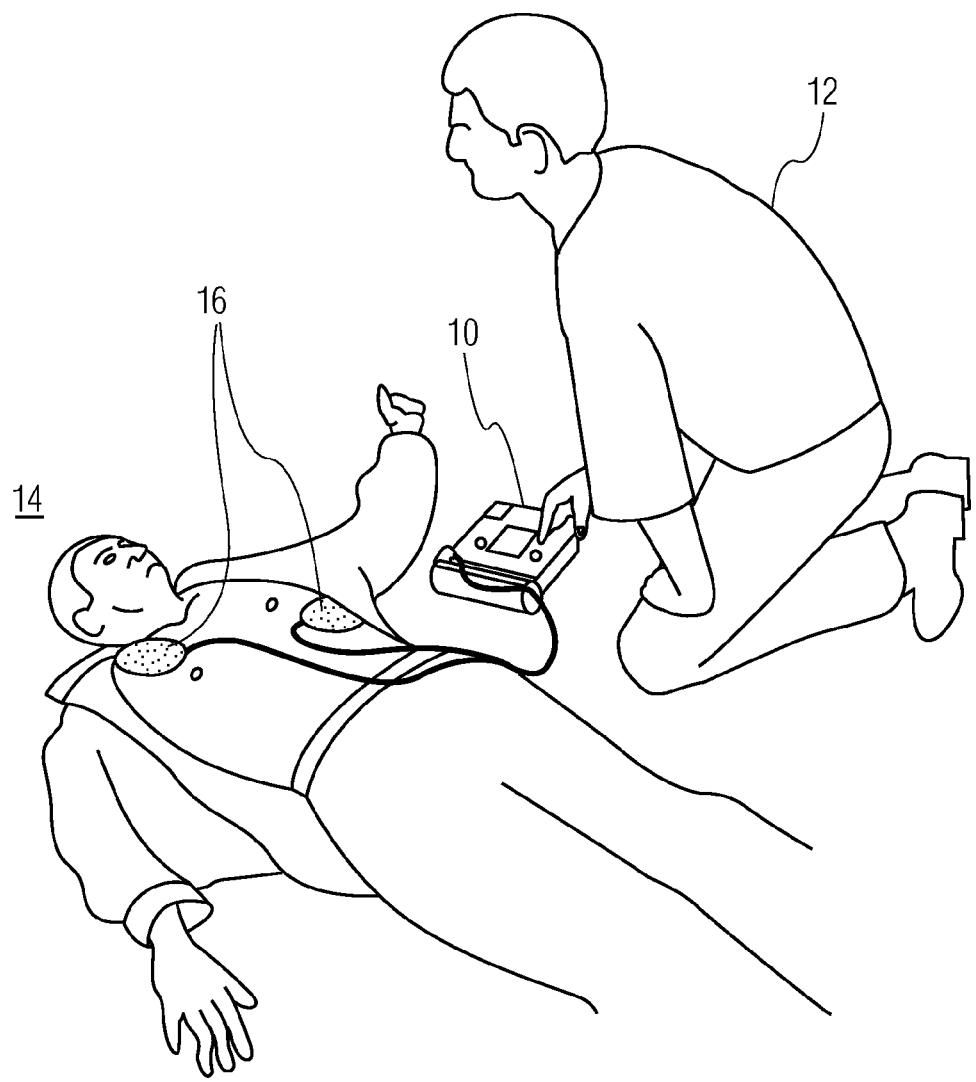
FIG. 1 is an illustration of a defibrillator being applied to a patient suffering from cardiac arrest.

FIG. 1 is an illustration of an AED 10 being applied by a user 12 to resuscitate a patient 14 suffering from cardiac arrest. In cardiac arrest, otherwise known as sudden cardiac arrest, the patient is stricken with a life threatening interruption to their normal heart rhythm, typically in the form of VF or VT that is not accompanied by a palpable pulse (i.e., shockable VT). In VF, the normal rhythmic ventricular contractions are replaced by rapid, irregular twitching that results in ineffective and severely reduced pumping by the heart. If normal rhythm is not restored within a time frame commonly understood to be approximately 8 to 10 minutes, the patient 14 will die. Conversely, the quicker defibrillation can be applied after the onset of VF, the better the chances that the patient 14 will survive the event.

A pair of electrodes 16 are applied across the chest of the patient 14 by the user 12 in order to acquire an ECG signal from the patients heart. The AED 10 then analyzes the ECG signal for signs of arrhythmia. If VF is detected, the AED 10 signals the user 12 that a shock is advised. After detecting VF or other shockable rhythm, the user 12 then presses a shock button on the AED 10 to deliver defibrillation pulse to resuscitate the patient 14.

Figure 4:
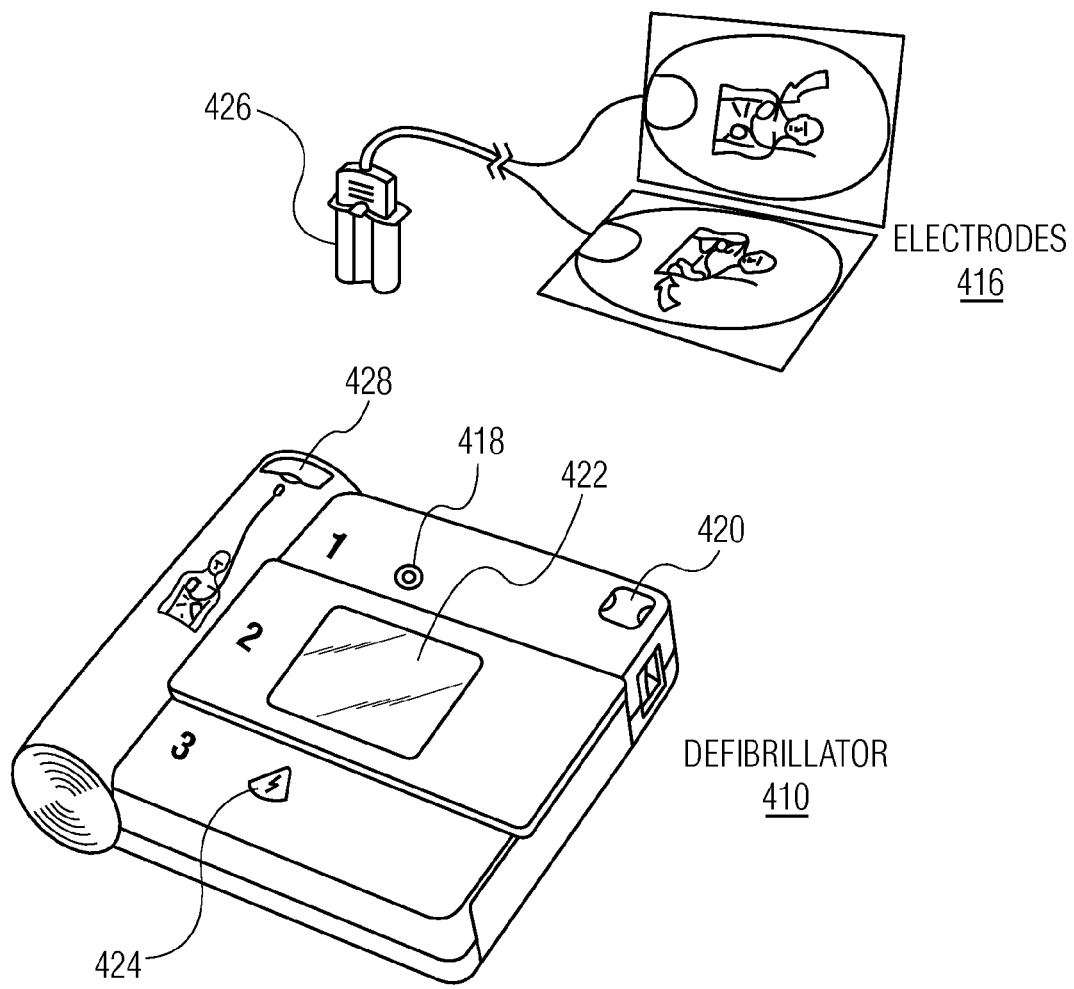
FIG. 4 is an illustration of a defibrillator and electrodes in which a combined monitor and CPR pause mode of operation according to an embodiment of the present invention can be implemented.

FIG. 4 illustrates a defibrillator according to an embodiment of the present invention. For purposes of the discussion that follows, the defibrillator is configured as an AED 410, and is designed for small physical size, light weight, and relatively simple user interface capable of being operated by personnel without high training levels or who otherwise would use the AED 110 only infrequently. In contrast, a paramedic or clinical defibrillator, on the other hand, tends to be larger, heavier, and have a more complex user interface capable of supporting a larger number of manual monitoring and analysis functions. Although the present embodiment of the invention is described with respect to application in an AED, other embodiments include application in different types of defibrillators, for example, manual defibrillators, and paramedic or clinical defibrillators.

A pair of electrodes 416 is connected to a connector 426 for insertion into a socket 428 on the AE D 410. Located on a top surface of the AED 410 is an on-off switch 418 that activates the AED 410 and begins the process of the prompting the user 12 (FIG. 1) to connect the electrodes 416 to the patient 14. A battery condition indicator 420 provides a continual visual indication of the defibrillator status and the available battery charge. A display 422 preferably provides for display of text such as user prompts and graphics such as ECG waveforms. A shock button 424 provides for delivery of the shock to the patient 14 if ECG analysis indicates that a shockable rhythm is present. Administration of defibrillation shocks is done by prompting the user 12 to manually press the shock button 424.

Figure 5:
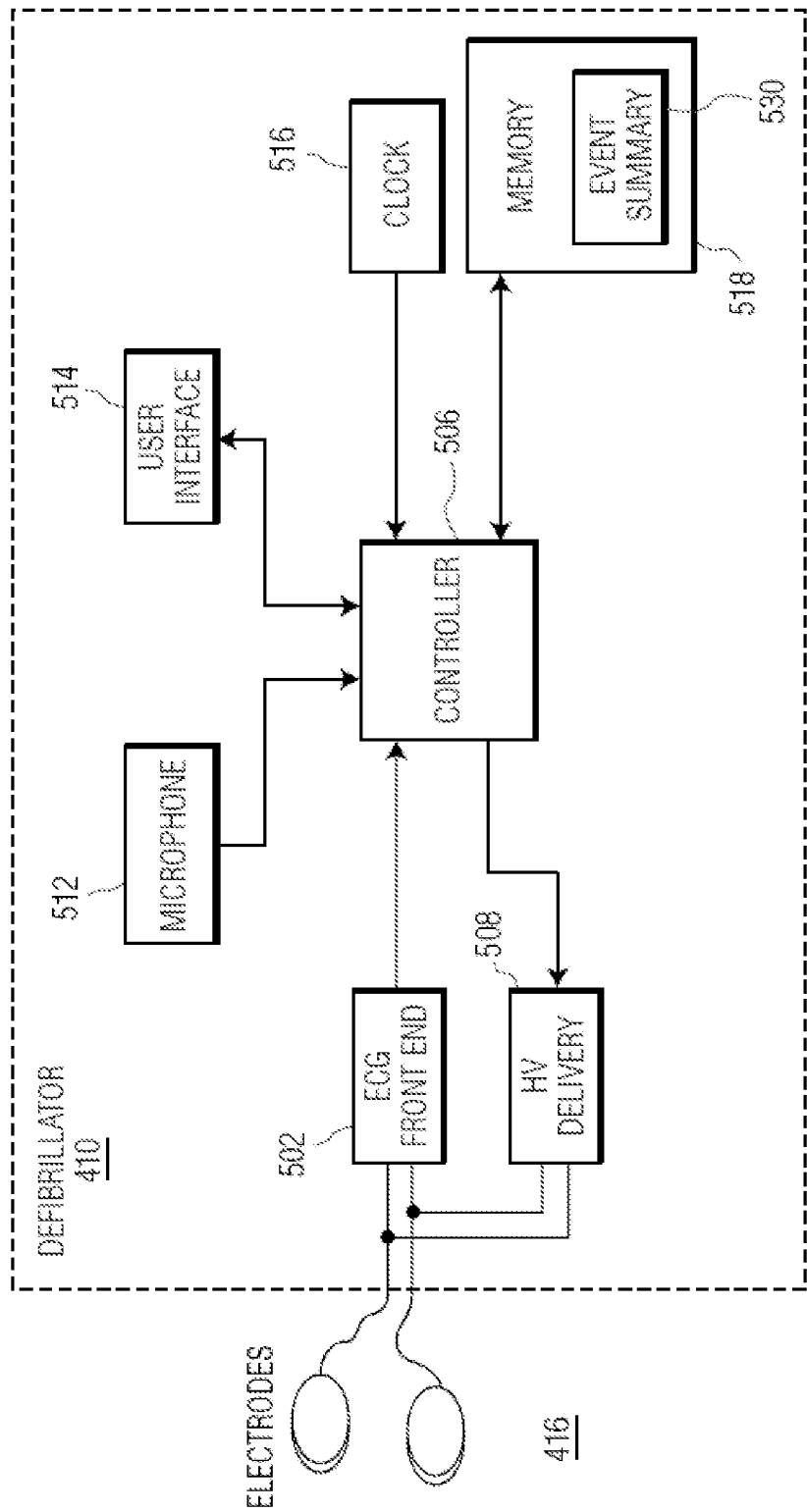
FIG. 5 is a is a simplified block diagram of the defibrillator of FIG. 4.

FIG. 5 is a simplified block diagram of the AED 410 (FIG. 4) according to an embodiment of the present invention. An ECG front end 502 is connected to the pair of electrodes 416 that are connected across the chest of the patient 14. The ECG front end 502 operates to amplify, buffer, filter and digitize an electrical ECG signal generated by the patient's heart to produce a stream of digitized ECG samples. The digitized ECG samples are provided to a controller 506 that performs an analysis to detect VF, shockable VT or other shockable rhythm. If a shockable rhythm is detected, the controller 506 sends a signal to HV delivery 508 to charge-up in preparation for delivering a shock. Pressing the shock button 424 then delivers a defibrillation shock from the HV delivery 508 to the patient 14 through the electrodes 416. As will be described in more detail below, the controller can be configured to implement a combined monitor and CPR pause mode of operation.

The controller 506 is coupled to further receive input from a microphone 512 to produce a voice strip. The analog audio signal from the microphone 512 is preferably digitized to produce a stream of digitized audio samples which may be stored as part of an event summary 530 in a memory 518. A user interface 514 may consist of the display 522, an audio speaker (not shown), and front panel buttons such as the on-off button 518 and shock button 524 for providing user control as well as visual and audible prompts. A clock 516 provides real-time clock data to the controller 506 for time-stamping information contained in the event summary 530. The memory 518, implemented either as on-board RAM, a removable memory card, or a combination of different memory technologies, operates to store the event summary 530 digitally as it is compiled over the treatment of the patient 14. The event summary 530 may include the streams of digitized ECG, audio samples, and other event data, as previously described.

Figure 6:
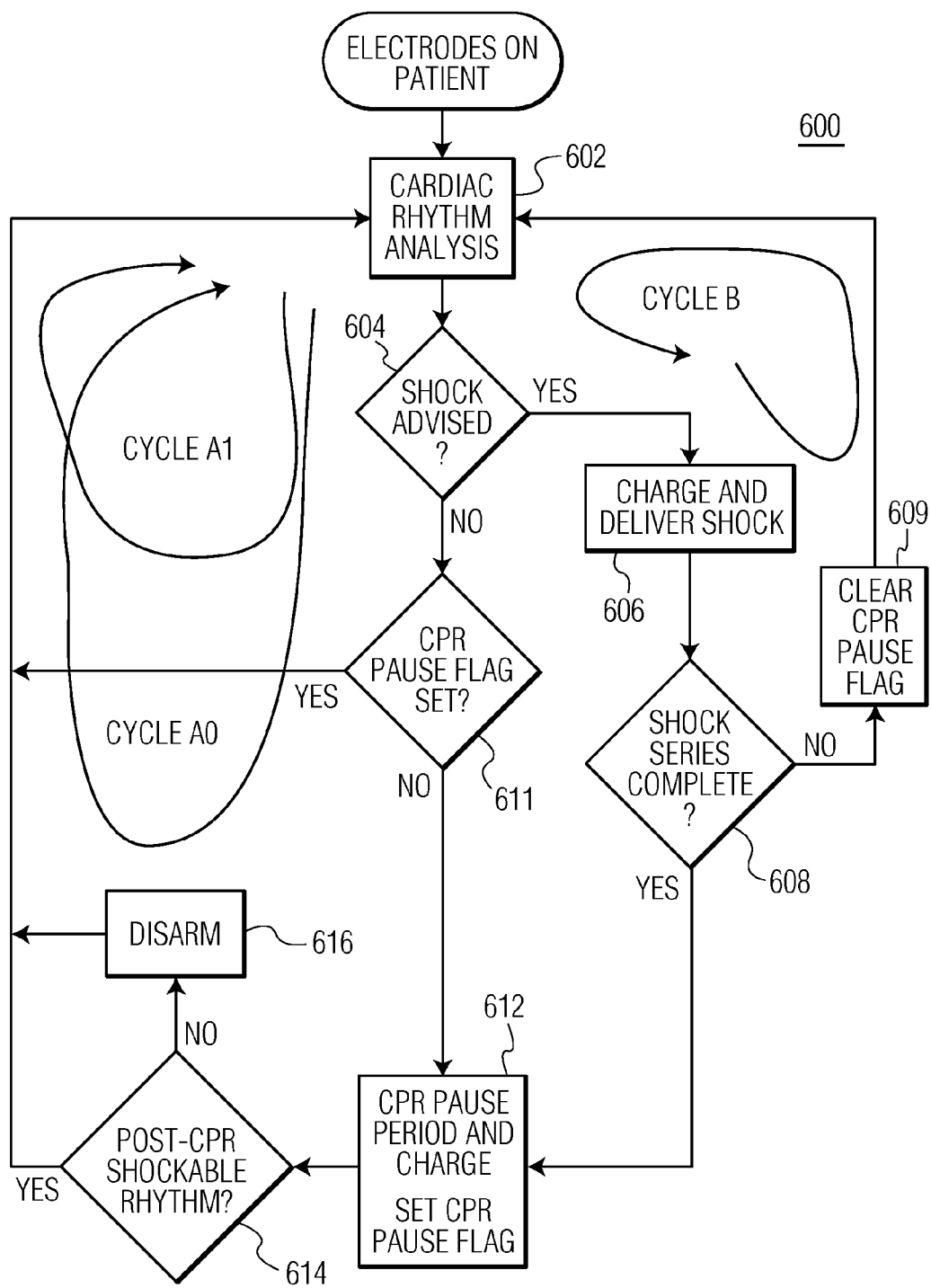
FIG. 6 is a flow diagram for an embodiment of a combined monitor and CPR pause mode of operation.

FIG. 6 is a flow diagram for a combined monitor and CPR pause mode of operation 600 that can be implemented by the AED 410 (FIGS. 4 and 5). Following attachment of electrodes 416 to the patient 14, the AED 410 analyzes the patient's cardiac rhythm at step 602. During the analysis, the AED 410 is precharged in preparation for delivery of electrotherapy. Based on the analysis at step 602, a determination is made at step 604 whether to advise the delivery of a defibrillation pulse. If delivery of a defibrillation pulse is advisable, such as when VF is detected in the patient's cardiac rhythm, at step 606 the AED 410 is fully charged and a defibrillation pulse is delivered to resuscitate the patient in response to pressing the shock button 424 on the AED 410.

Figure 2:
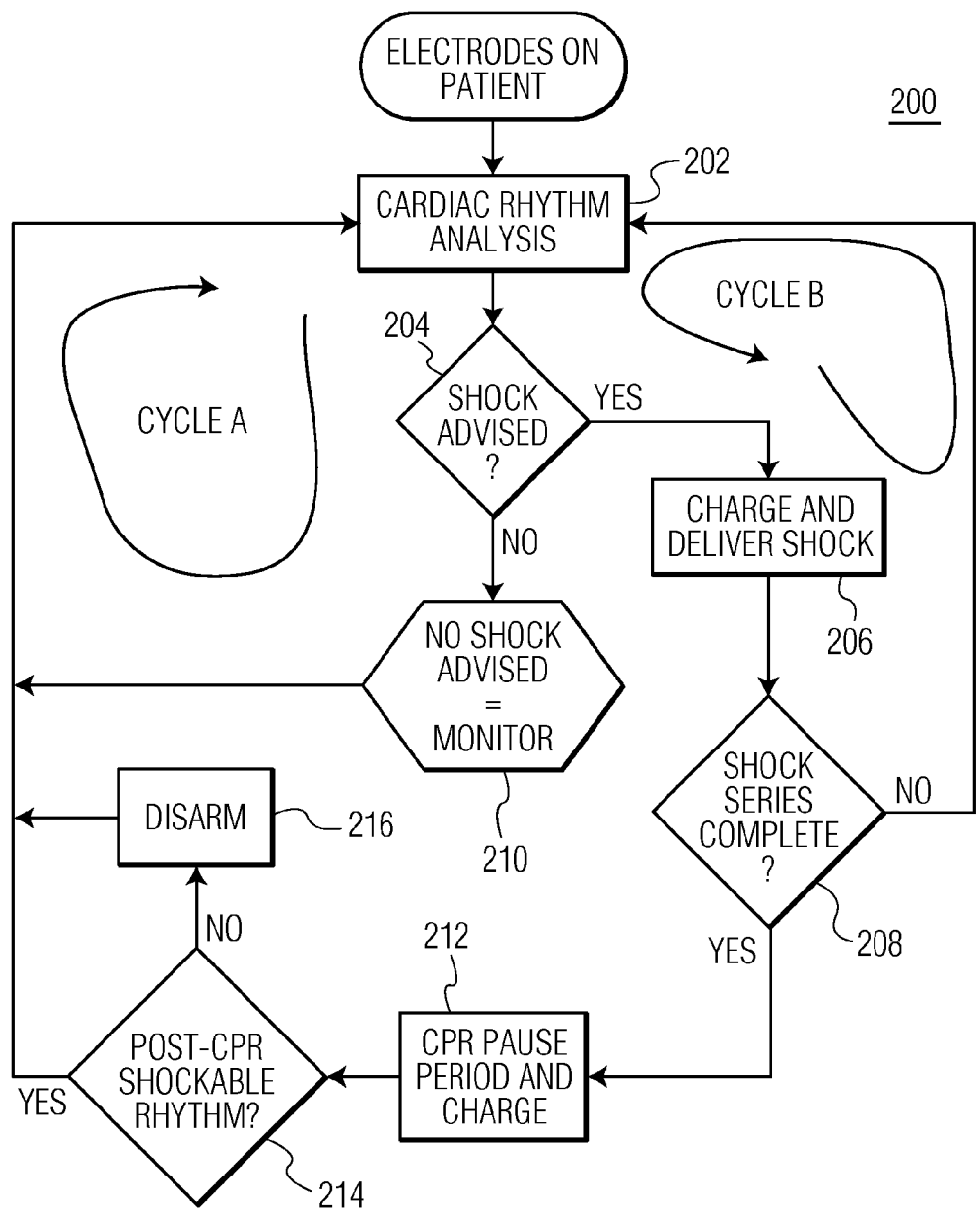
FIG. 2 is a flow diagram of a conventional monitor mode of operation.

As with the modes of operation 200 and 300 (FIGS. 2 and 3), at step 608 the AED 410 determines whether a series of defibrillation pulses has been delivered, and if so, a CPR pause period is entered at step 612. However, if the series of defibrillation pulses has not been delivered, a CPR pause flag, which is set if a CPR pause period has been performed, is cleared at step 609. As will be explained in more detail below, clearing the CPR pause flag allows at least one CPR pause to occur following successful resuscitation of the patient 14. The patient's cardiac rhythm is again analyzed at step 602 to determine if a normal cardiac rhythm has been restored by the electrotherapy or whether a shockable rhythm is still present. The process of analyzing the patient's cardiac rhythm, determining that delivery of a defibrillation pulse is advised, and delivering the defibrillation pulse is labeled in FIG. 6 as "cycle B."

Assuming that a normal cardiac rhythm is restored, delivery of a defibrillation pulse will not be advised at step 604, and at step 611, the condition of the CPR flag is checked. As previously discussed, assuming that a defibrillation pulse was delivered and successfully resuscitated the patient, the CPR flag is not set. Consequently, a CPR pause period is entered at step 612 and the CPR flag is then set.

As with the modes of operation 200 and 300, during the CPR pause period at step 612, audio and/or visual prompts are used to instruct the user 12 to perform uninterrupted CPR on the patient 14, which is typically on the order of one minute. During the CPR pause period, the AED 410 is precharged in preparation for delivery of a defibrillation pulse, if necessary. Following the completion of the CPR pause period, the patient's cardiac rhythm is analyzed for a shockable rhythm at step 614. If a shockable rhythm is detected, the patient's cardiac further analyzed at step 602 to determine if delivery of another defibrillation pulse is advised. However, if a shockable rhythm is not detected at step 614, which can indicate that the patient 14 has stabilized and a normal cardiac rhythm has been restored, the AED 410 is disarmed at step 616, which includes discharging the precharge from step 612, before further analyzing the patient's cardiac rhythm at step 602. The process of analyzing the patient's cardiac rhythm, determining that a defibrillation pulse is not advisable and entering the CPR pause period is labeled in FIG. 6 as "cycle A0."

Following the CPR pause period from step 612, at which time the CPR flag was set, and assuming that at step 604 delivery of a defibrillation pulse is not advisable because the patient 14 has been resuscitated and normal cardiac rhythm has been restored, operation will loop back to analysis of the patient's cardiac rhythm at step 602 and repeat through step 611. The process of analyzing the patient's cardiac rhythm, determining that a defibrillation pulse is not advisable, and then looping back to analyzing the patient's cardiac rhythm is labeled in FIG. 6 as "cycle A1." Cycle A1 will continue to loop until analysis of the patient's cardiac rhythm suggests that delivery of a defibrillation pulse is advisable at step 604, at which time, cycle B is performed. Such a situation occurs if a patient who exhibited signs of stabilizing refibrillates and electrotherapy is needed again.

The combined monitor and CPR pause mode of operation 600 provides a CPR pause period following the delivery of a complete series of defibrillation pulses and also following the delivery of a defibrillation pulse and a determination that delivery of a further defibrillation pulse is not advisable, such as when a patient is resuscitated. A subsequent consecutive "no shock advised" results in the AED 410 entering a loop (cycle A1) where the patient's cardiac rhythm is continuously monitored. During the cycle A1, the patient's cardiac rhythm continues to be monitored without the precharging/discharging cycle that occurs for continuously looping through a CPR pause period (cycle A0), as in the CPR pause mode of operation 300 (FIG. 3), thereby saving battery life. If, however, during the cycle A1, delivery of a defibrillation pulse is advised at step 604, cycle B is entered in which the defibrillation pulse is delivered and the CPR pause flag is cleared so that the next occurrence of a no-shock advised at step 604 will provide a CPR pause period at step 612 for administration of uninterrupted CPR.

Figure 3:
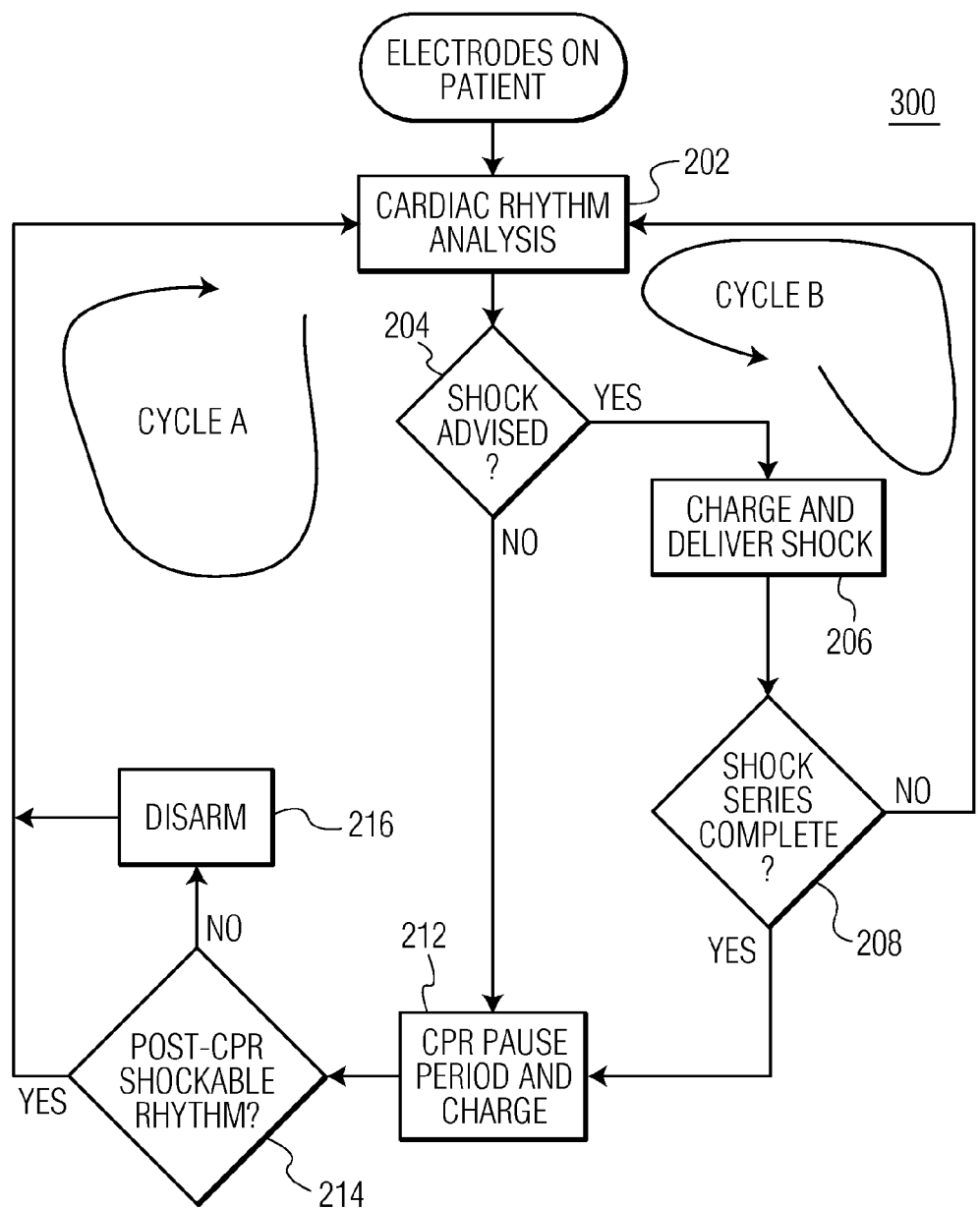
FIG. 3 is a flow diagram of a conventional CPR pause mode of operation.
Figure 7:
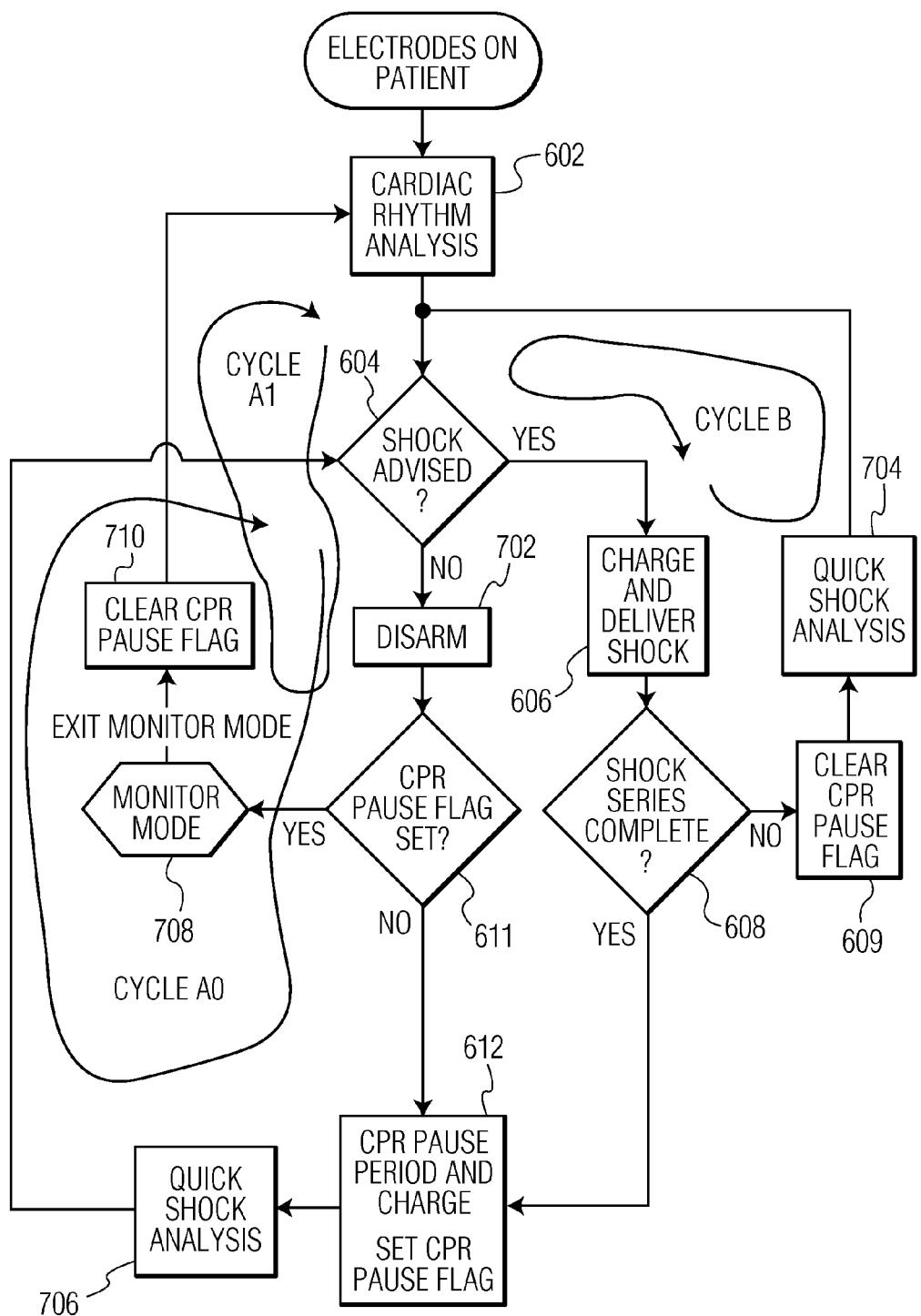
FIG. 7 is a flow diagram of another embodiment of a combined monitor and CPR pause mode of operation.

FIG. 7 is flow diagram for another embodiment of a combined monitor and CPR pause mode of operation that can be implemented by the AED 410. The mode of operation 700 combines a monitor mode of operation, such as that previously described with respect to the monitor mode of operation 200 (FIG. 2), and a CPR pause mode of operation, such as that previously described with respect to the CPR pause mode 300 (FIG. 3). The mode of operation 700 includes various process steps that were previously described with respect to the mode of operation 600 (FIG. 6).

With reference to FIG. 7, following attachment of electrodes 416 to the patient 14, the AED 410 analyzes the patient's cardiac rhythm at step 602. During the analysis, the AED 410 is precharged in preparation for delivery of electrotherapy. Based on the analysis at step 602, a determination is made at step 604 whether to advise the delivery of a defibrillation pulse. If delivery of a defibrillation pulse is advisable, such as when VF is detected in the patient's cardiac rhythm, at step 606 the AED 410 is fully charged and a defibrillation pulse is delivered to resuscitate the patient 14 in response to pressing the shock button on the AED 410.

As with the mode of operation 600, at step 608 the AED 410 determines whether a series of defibrillation pulses has been delivered, and if so, a CPR pause period is entered at step 612. However, if the series of defibrillation pulses has not been delivered, a CPR pause flag, which is set if a CPR pause period has already been performed, is cleared at step 609. Additionally, in the mode of operation 700, a relatively short shock analysis is performed at step 704 on the patient 14 following delivery of the defibrillation pulse. A short shock analysis can be performed shortly after the delivery of the defibrillation pulse because at that time, it is likely that activity that can interfere with analysis of the patient's cardiac rhythm has ceased, for example, moving the patient or administering CPR compressions. The short shock analysis at step 704 is in contrast to the cardiac rhythm analysis at step 602, which is performed after audio and/or visual prompts have been given to direct the user 12 to stand clear of the patient 14 and waits until a time period has elapsed before beginning analysis to allow the user 12 to move away and the patient 14 to come to rest. While the quick shock analysis at step 704 is performed, the AED 410 is precharged in preparation for delivery of another defibrillation pulse, if necessary. The process of determining that delivery of a defibrillation pulse is advisable, delivering the defibrillation pulse, and performing a quick shock analysis is labeled in FIG. 7 as "cycle B."

A determination is made at step 604 whether delivery of another defibrillation pulse is advisable. If not advisable, the AED 410 is disarmed at step 702 which, as previously discussed, includes discharging the precharge developed while the quick shock analysis at step 704 is performed. Assuming that a defibrillation pulse has been delivered, and normal cardiac rhythm has been restored, at step 611 the CPR pause flag is not be set (cleared at step 609) and a CPR pause period will be entered at step 612 to provide a time period for uninterrupted administration of CPR. Additionally, as previously discussed, the AED 410 is precharged to prepare for delivery of a defibrillation pulse in the event it is necessary. The CPR pause flag is also set at step 612 to indicate that at least one CPR pause period has been performed.

After the CPR pause period has elapsed, a quick shock analysis is performed at step 706. As with the quick shock analysis performed at step 704, the analysis can begin shortly after the CPR pause period has ended because it is likely that at that time the user 12 will cease administering CPR and move away from the patient 14. Audio and/or visual prompts can be given toward the end of the CPR pause period to ensure that the activity has ceased to allow the quick shock analysis to be performed. A determination whether delivery of a defibrillation pulse is advisable is made at step 604 following the quick shock analysis at step 706. The process of determining that a defibrillation pulse is not advisable, entering the CPR pause period, and performing the quick shock analysis is labeled in FIG. 6 as "cycle A0."

In response to a subsequent consecutive occurrence of advising not to deliver a defibrillation pulse at step 604, the AED 410 is disarmed at step 702 to discharge the precharge from step 612, and because the CPR flag was set at step 612 due to entering the CPR pause period, a monitor mode is entered at step 708. The process of analyzing the patient's cardiac rhythm, determining that a defibrillation pulse is not advisable, and then entering the monitor mode is labeled in FIG. 7 as "cycle A1." The monitor mode can be conventional, during which the patient's cardiac rhythm is monitored for characteristics, such as defibrillation, indicating that the patient 14 may need electrotherapy. The AED 410 will remain in the monitor mode until an event suggests that delivery of a defibrillation pulse is detected. As previously discussed, this can occur when a patient that has initially been stabilized experiences a recurrence of arrhythmia. In the event of such an occurrence, the monitor mode is exited and the CPR flag is cleared at step 710. As a result, following analysis of the patient's cardiac rhythm at step 602 and in response to the next occurrence of advising not to deliver a defibrillation pulse, a CPR pause period can be entered again to allow for uninterrupted administration of CPR. Unlike the quick shock analysis at steps 704 and 706, after exiting the monitor mode the analysis of the cardiac rhythm at step 602 begins after a delay to provide sufficient time for activity around the patient to cease.

The combined monitor and CPR pause mode of operation 700 provides a CPR pause period following the delivery of a complete series of defibrillation pulses and following an initial occurrence of "no-shock advised." A subsequent consecutive occurrence of no shock advised results in the AED 410 entering a monitor mode (cycle A1) where the patient's cardiac rhythm is continuously monitored without the precharging/discharging cycle that occurs for continuously looping through a CPR pause period (cycle A0), which as previously discussed, saves battery life. If, however, the monitor mode is exited due to the detection of a fibrillation event, the CPR flag is cleared so that the next occurrence of a no-shock advised at 604 will provide a CPR pause period.

From the foregoing it will be appreciated that, although specific embodiments of the invention have been described herein for purposes of illustration, various modifications may be made without deviating from the spirit and scope of the invention. For instance, other decision points may be used in the treatment protocol. For example, after a determination that no shock is advices (step 604) and the AED is disarmed (step 702), the patient's heartrate may be analyzed. If the heartrate is in excess of thirty beats per minute, indicating good blood flow, the AED will enter the monitor mode (step 708). But if the heartrate is below thirty beats per minutes the AED commences a CPR pause period (step 612). Accordingly, the invention is not limited except as by the appended claims.

What is claimed is:

1. A method for providing electrotherapy, comprising:
analyzing a cardiac signal for a shockable rhythm;
delivering electrotherapy from a high-voltage energy source if a shockable rhythm exists;
pausing for a non-interruptible CPR period after analyzing the cardiac signal;
precharging the high-voltage energy source during the non-interruptible CPR period;
after the pausing step, re-analyzing the cardiac signal for a shockable rhythm; and
after the re-analyzing step, monitoring the cardiac signal without precharging the high-voltage energy source, the monitoring step being interruptible.

2. The method of claim 1 wherein pausing for a non-interruptible CPR period is preceded by a determination that no shock is advised, and monitoring the cardiac signal is preceded by a second determination that no shock is advised.

3. The method of claim 2 wherein pausing for the non-interruptible CPR period occurs in response to a first determination that a shockable rhythm does not exist and wherein monitoring the cardiac signal occurs in response to a second consecutive determination that a shockable rhythm does not exist.

4. The method of claim 1, further comprising discharging the high-voltage energy source in response to not detecting a shockable rhythm from re-analyzing the cardiac signal.

5. The method of claim 1, further comprising monitoring the cardiac signal in response to a determination that a shockable rhythm does not exist and a heart rate in excess of a predetermined value is identified, and pausing for a non-interruptible CPR period in response to a determination that a shockable rhythm does not exist and a heart rate less than the predetermined value is identified.

* * * * *